United States Patent [19]

Grof

[11] Patent Number: 4,867,981
[45] Date of Patent: Sep. 19, 1989

[54] TAPE RELEASING COMPOSITION AND METHOD OF USING SAME

[75] Inventor: Tibor Grof, Seabrook, Md.

[73] Assignee: Henry Greenwald, Silver Spring, Md.

[21] Appl. No.: 122,433

[22] Filed: Nov. 19, 1987

[51] Int. Cl.$^4$ ............................ A61F 13/00; B08B 3/08
[52] U.S. Cl. ................................. 424/443; 424/448; 428/40; 428/352
[58] Field of Search .................. 428/40, 352, 447; 424/448, 443, 447, 445; 524/379, 385, 389, 364, 588; 106/287.14

[56] References Cited

U.S. PATENT DOCUMENTS

| | | |
|---|---|---|
| 2,736,721 | 2/1956 | Dexter . |
| 2,751,314 | 6/1956 | Keil . |
| 2,882,183 | 4/1959 | Bond et al. . |
| 2,985,554 | 5/1961 | Dickard . |
| 3,247,845 | 4/1966 | Kennedy . |
| 3,339,546 | 9/1967 | Chen . |
| 3,627,559 | 6/1969 | Chen . |
| 3,936,571 | 2/1976 | Van Hoof et al. . |
| 4,299,741 | 11/1981 | Doehnert ............................ 524/364 |
| 4,311,763 | 1/1982 | Conroy ............................... 524/364 |
| 4,324,595 | 4/1982 | Kasprzak ............................ 134/38 |
| 4,374,884 | 2/1983 | Kwok et al. . |
| 4,496,687 | 1/1985 | Okada et al. ....................... 524/859 |
| 4,598,004 | 7/1986 | Heinecke ............................ 428/40 |
| 4,624,870 | 11/1986 | Anthony ............................. 524/389 |
| 4,684,557 | 8/1987 | Pennace et al. ...................... 428/40 |
| 4,728,571 | 3/1988 | Clemens et al. ..................... 428/354 |

FOREIGN PATENT DOCUMENTS 1176932 10/1984 Canada .

*Primary Examiner*—Nancy A. B. Swisher
*Attorney, Agent, or Firm*—Shoemaker and Mattare, Ltd.

[57] ABSTRACT

The present invention is related to new tape releasing compositions and methods of using the same. The tape releasing composition comprises a fluid mixture of a non-reactive component, a penetrant and a soluble adhesive releasing agent in such amounts that the resulting composition is non-toxic and non-irritating to skin and allows tension-free removal of an adhesive tape from skin without sticky deposit or injury to the skin.

3 Claims, No Drawings

TAPE RELEASING COMPOSITION AND METHOD OF USING SAME

BACKGROUND OF THE INVENTION

1. Technical Field

The present invention is related generally to composition of matter and the method of using same. More particularly, the present invention is related to tape releasing compositions which allow residue-free separation of a pressure-sensitive adhesive tape from a surface without injury or damage to the surface. Although the instant inventive concepts have general application, they are particularly useful in removing pressure-sensitive tapes from skin, especially removing surgical tapes from the human body.

2. State of the Art

Separation of pressure-sensitive adhesive tapes from surfaces, such as human or animal skin, particularly from rough or pubescent surfaces and especially human or animal skin containing open wounds or healing trauma, is usually difficult requiring great care and sensitivity to avoid pain and further damage to the surface. In case of repeated application and removal of the tape from the same skin area, it might induce severe irritation and often blisters which might result in an open skin damage. Furthermore, in case of wounds or skin, removal of such tape by prior art techniques usually pulls hair from the skin causing great discomfort and frequently leaves a residue of the adhesive composition which is usually difficult to remove due to its tackiness.

Solvents such as alcohols and the like, have been used to assist in releasing such tapes, but such treatment commonly leaves a sticky deposit or residue which must be removed from the surface after the tape has been lifted away. All such techniques become particularly problematic or hazardous in surgical, fracture or wound areas where the least possible disturbance to the tissue is desired.

Athletes commonly tape certain areas of their body during sporting events to protect themselves against injury and removing such tape becomes a tedious chore particularly since the tape is generally applied in multiple layers increasing the adhesive material that must be released. The instant inventive concepts facilitate removal of tape in such situations and permit the areas to be quickly retaped if desired.

SUMMARY OF THE INVENTION

It is, therefore, an object of the present invention to provide a tape releasing composition allowing tensionless, easy and residue-free separation of adhesive tape from a surface to which the tape is adhering.

It is a further object of the present invention to provide a method of releasing pressure-sensitive adhesive tape from a surface comprising contacting the interface between an adhesive tape and a surface to which said tape is adhering, with a tape-releasing amount of the composition of the present invention, and removing said tape tensionlessly from said surface without leaving residue and without deleteriously affecting the tape or the surface and permitting substantially immediate reapplication of tape to the same surface.

Other objects and advantages of the present invention will become evident from the following Detailed Description of the Invention.

DETAILED DESCRIPTION OF THE INVENTION

The above and various other objects and advantages of the present invention are achieved by a composition of matter, comprising a fluid mixture of a non-reactive liquid component, a penetrant, and an adhesive releasing agent in such amounts that the resulting composition is non-toxic and non-irritating to the skin and allows tension-free removal of a pressure sensitive adhesive tape without sticky deposit or injury to the skin.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "non-reactive" as used herein means the component is miscible with the "penetrant" and "releasing agent", vide infra, and is inert to the adhesive layer of the tape. Preferred examples of such non-reactive agents are water, polyalkylene glycol and the like.

A "penetrant" is an agent which, when applied to a surface, such as that of an adhesive tape, quickly (almost instantaneously) penetrates or permeates through the tape material and reaches to the adhesive layer of the adhesive tape. Another important characteristic of the penetrant is that it has little or no solvency and plasticizing effect on the adhesive layer in contrast to other penetrating liquids, such as methyl ethyl ketone, mineral spirits and the like, which have solvency and/or plasticizing effect on the adhesive layer, and because of it they belong to the adhesive releasing agent group. Preferred examples of such "penetrant" are ethanol, isopropyl alcohol, octyl- or nonyl-phenoxy polyethoxy ethanol and the like.

An "adhesive releasing agent" is a compound which almost instantaneously releases the bond between the skin and the adhesive material of the tape allowing almost effortless removal of the tape without leaving any residual sticky deposit on the skin and without causing painful shearing force on the hairs, if present on the skin. The members of this group are all either excellent solvents or strong plasticizers for the adhesive layer of the tape. It is noted that the proper ratio of the "non reactive" and "adhesive release agent" is critical because it is this ratio which provides a balance combination of simultaneous "dissolving" and "precipitating" effect on the rubbery adhesive layer. Preferred examples of the adhesive releasing agent are silicone compounds, such as polyalkylene modified dimethylpolysiloxane, dimethyl ketone, methyl ethyl ketone, mineral spirits, alkylated aromatics and the like.

The mixture of the present invention may range from a homogeneous solution to an emulsion. If an emulsion, a surfactant such as coconut amphoteric, nonylphenoxy polyethoxy ethanol, octylphenoxy polyethoxy ethanol and the like could be employed to stabilize the suspension phase.

Other adjuvants or additives such as defoamers, sterilants, antiseptic or antibiotic agents, perfumes, colorants, analgesic or anesthetic agents and the like and mixtures thereof well known to one of ordinary skill in the art could, of course, also be included either alone or in combination, in the formulation of the tape releasing composition of the present invention. The formulation could be applied in any suitable manner such as with a swab, a dropper, a sprayer and the like. It could be applied on top of the tape if the tape is permeable to the composition which most surgical-type tapes are, or to the underside of the adhesive surface in the interface above the skin by slightly lifting the tape in one corner, if the tape is impermeable to the composition. In this latter instance, it has been found that the composition of the instant invention quickly flows under the tape by capillary action to facilitate ready removal of the tape without injury to the underlying surface.

Without being bound to any particular theory, it is postulated that upon contact with the tape releasing composition, the adhesive material is plasticized and softened thereby abating the bonding force between the adhesive surfaces, resulting in easy and painless lifting off the tape. Due to the low surface tension, the composition spreads almost instantaneously in the interface and the releasing action takes place quickly. It is noted that due to the absence of sticky residues after removal of the adhesive tape, fresh or new adhesive tape can be immediately applied on the same surface. Thus repeated or multiple applications of the tape poses no problem.

Preferred examples of the composition of the present invention are now illustrated.

EXAMPLE 1

|  | RANGE | PREFERRED |
|---|---|---|
| (1) Water about | 40-90%/vol | 80%/vol |
| (2) Ethanol about | 5-30%/vol | 15%/vol |
| (3) Polyalkylene modified dimethylpolysiloxane about | 3-40%/vol | 5%/vol |
| TOTAL | 100%/vol | 100%/vol |

EXAMPLE 2

|  | PREFERRED | RANGE |
|---|---|---|
| (1) Water | 25%/vol | 15-50%/vol |
| (2) Mineral spirits | 54%/vol | 30-70%/vol |
| (3) Nonylphenoxy polyethoxy ethanol | 7.5%/vol | 5-15%/vol |
| (4) Octylphenoxy polyethoxy ethanol | 5%/vol | 2-20%/vol |
| (5) Isopropyl Alcohol | 8.5%/vol | 4-20%/vol |
| TOTAL | 100%/vol | 100%/vol |

EXAMPLE 3

|  | PREFERRED | RANGE |
|---|---|---|
| (1) Propylene Glycol | 15%/vol | 5-30%/vol |
| (2) Water | 83.6%/vol | 25-90%/vol |
| (3) Coconut Amphoteric | 0.7%/vol | 0.1-10%/vol |
| (4) Polyalkylene Modified Dimethylpolysiloxane | 0/7%/vol | 0.1-10%/vol |
| (5) Silicone defoamer | 0.01%/vol | 0.01-0.5%/vol |
| TOTAL | 100%/vol | 100%.vol |

EXAMPLE 4

|  | PREFERRED | RANGE |
|---|---|---|
| (1) Water | 85%/vol | 30-90%/vol |
| (2) Methyl Ethyl Ketone | 10%/vol | 5-30%/vol |
| (3) Ethyl alcohol | 5%/vol | 2-15%/vol |
| TOTAL | 100%/vol | 100%/vol |

EXAMPLE 5

|  | PREFERRED | RANGE |
|---|---|---|
| (1) Propylene Glycol | 15%/vol | 5-30%/vol |
| (2) Polypropylene Glycol (Mol. Wt. 400) | 83.6%/vol | 62-95%/vol |
| (3) Coconut Amphoteric | 0/7%/vol | 0.1-5%/vol |
| (4) Polyalkylene Modified Dimethypolysiloxane | 0.7%/vol | 0.1-10%/vol |
| TOTAL | 100%/vol | 100%/vol |

It should be noted that the tape releasing composition of the present invention has been tested with virtually every type of commercially available pressure-sensitive adhesive tapes which are usually made of a porous and/or non-porous fabric material with a pressure sensitive adhesive layer applied to said fabric material. Typical examples of such tapes are surgical adhesive tapes, adhesive bandages and the like. When sprayed or applied on top of a typical commercially available adhesive tape, the composition of the present invention quickly permeates through the porous fabric and allows effortless, clean and easy removal of the tape from the adhering surface. In the event that the adhesive tape is made of a non-permeable material, the same result is obtained by applying the composition of the present invention directly in the interface by slightly lifting the tape in one corner over the skin or the surface.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of releasing adhesive bandage material adhering to skin, comprising the steps of contacting the interface between an adherent adhesive bandage material and the surface of skin to which said adhesive is adhering, with a releasing amount of a composition comprising a fluid mixture consisting essentially of a non-reactive component, a penetrant and a soluble adhesive releasing agent and then removing said tape from said surface without leaving substantial adhesive residue and without deteriously affecting the bandage material or the surface of the skin.

2. The method of claim 1 applying said composition to the top of the bandage material, when said material is permeable to said composition.

3. The method of claim 1 applying said composition directly to the interface between the adhesive layer of the bandage material and the surface of the skin, where said material is impermeable to said composition.

* * * * *